United States Patent
Wajima et al.

(10) Patent No.: US 9,763,869 B2
(45) Date of Patent: Sep. 19, 2017

(54) HYDROPHILIC THICKENER AND COSMETIC COMPOSITION

(71) Applicant: SUMITOMO SEIKA CHEMICALS CO., LTD., Kako-gun, Hyogo (JP)

(72) Inventors: Ayami Wajima, Himeji (JP); Junichi Mizukawa, Himeji (JP); Tsuyoshi Masuda, Himeji (JP); Hitoshi Ozawa, Osaka (JP)

(73) Assignee: SUMITOMO SEIKA CHEMICALS CO., LTD., Kako-Gun, Hyogo (JP)

( * ) Notice: Subject to any disclaimer, the term of this patent is extended or adjusted under 35 U.S.C. 154(b) by 0 days.

(21) Appl. No.: 14/901,267

(22) PCT Filed: Jun. 6, 2014

(86) PCT No.: PCT/JP2014/065114
§ 371 (c)(1),
(2) Date: Dec. 28, 2015

(87) PCT Pub. No.: WO2014/208316
PCT Pub. Date: Dec. 31, 2014

(65) Prior Publication Data
US 2016/0367465 A1 Dec. 22, 2016

(30) Foreign Application Priority Data
Jun. 28, 2013 (JP) .................. 2013-136521

(51) Int. Cl.
C08F 12/30 (2006.01)
C08F 20/00 (2006.01)
(Continued)

(52) U.S. Cl.
CPC .............. *A61K 8/8147* (2013.01); *A61K 8/86* (2013.01); *A61Q 1/02* (2013.01); *A61Q 5/06* (2013.01);
(Continued)

(58) Field of Classification Search
CPC .............................. A61K 8/044; A61K 47/10
(Continued)

(56) References Cited

U.S. PATENT DOCUMENTS

| | | | |
|---|---|---|---|
| 4,929,690 A | 5/1990 | Goertz et al. | |
| 5,256,737 A | 10/1993 | Barzaghi | |

(Continued)

FOREIGN PATENT DOCUMENTS

| | | |
|---|---|---|
| JP | 1-149805 A | 6/1989 |
| JP | 4-218582 A | 8/1992 |

(Continued)

OTHER PUBLICATIONS

International Search Report mailed Sep. 16, 2014, in PCT International Application No. PCT/JP2014/065114.
(Continued)

*Primary Examiner* — William Cheung
(74) *Attorney, Agent, or Firm* — Birch, Stewart, Kolasch & Birch, LLP

(57) ABSTRACT

A hydrophilic thickener comprising a polymer obtainable by subjecting a water-soluble ethylenically unsaturated monomer to a reversed phase suspension polymerization in the presence of a polyoxyethylene polyoxypropylene alkyl ether; and a cosmetic composition containing the hydrophilic thickener. The hydrophilic thickener according to the present invention can be used in the fields of cosmetics such as powder foundations, liquid foundations, emulsions, lotions, liquid cosmetics, moisturizing gel, all-in-one gels, cleansing foams, hair setting agents, emollient creams; toiletries, sundries, and the like.

8 Claims, 2 Drawing Sheets

(51) Int. Cl.
*C08F 20/06* (2006.01)
*A61K 8/81* (2006.01)
*A61Q 19/00* (2006.01)
*A61K 8/86* (2006.01)
*C08F 2/32* (2006.01)
*C08F 4/04* (2006.01)
*C08F 220/56* (2006.01)
*C08F 2/18* (2006.01)
*C08F 220/54* (2006.01)
*A61Q 1/02* (2006.01)
*A61Q 5/06* (2006.01)
*A61Q 19/10* (2006.01)
*C08F 120/06* (2006.01)

(52) U.S. Cl.
CPC .............. *A61Q 19/00* (2013.01); *A61Q 19/10* (2013.01); *C08F 2/18* (2013.01); *C08F 2/32* (2013.01); *C08F 4/04* (2013.01); *C08F 120/06* (2013.01); *C08F 220/54* (2013.01); *C08F 220/56* (2013.01); *A61K 2800/10* (2013.01); *A61K 2800/48* (2013.01)

(58) Field of Classification Search
USPC .................................. 526/289, 303.1, 317.1
See application file for complete search history.

(56) References Cited

U.S. PATENT DOCUMENTS

| | | |
|---|---|---|
| 5,684,107 A | 11/1997 | Schneider et al. |
| 2005/0175564 A1 | 8/2005 | Kaneda et al. |
| 2007/0219315 A1 | 9/2007 | Braun |
| 2009/0182092 A1 | 7/2009 | Yokoyama et al. |
| 2010/0029787 A1 | 2/2010 | Kaneda et al. |
| 2011/0098231 A1* | 4/2011 | Omura .................. A61K 8/042 514/18.8 |
| 2013/0096205 A1 | 4/2013 | Murata |

FOREIGN PATENT DOCUMENTS

| | | |
|---|---|---|
| JP | 3115321 B2 | 12/2000 |
| JP | 2004-43785 A | 2/2004 |
| JP | 2006-52319 A | 2/2006 |
| JP | 2007-509217 A | 4/2007 |
| JP | 2007-284389 A | 11/2007 |
| JP | 2010-64986 A | 3/2010 |
| WO | WO 2011/149006 A1 | 12/2011 |
| WO | WO 2013/018491 A1 | 2/2013 |

OTHER PUBLICATIONS

Extended European Search Report dated Oct. 6, 2016, for European Application No. 14817573.0.

* cited by examiner

[FIG. 1]
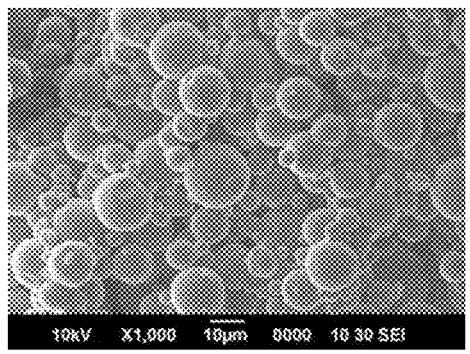
[FIG. 2]

[FIG. 3]
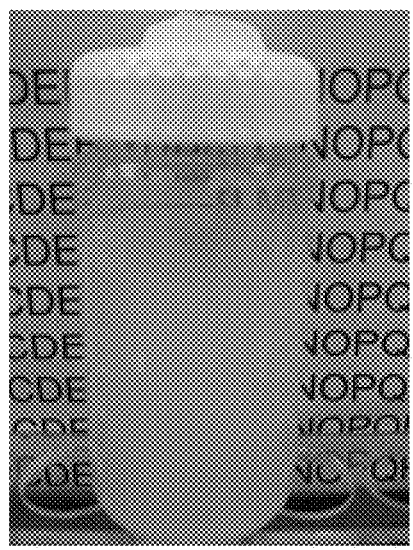
[FIG. 4]
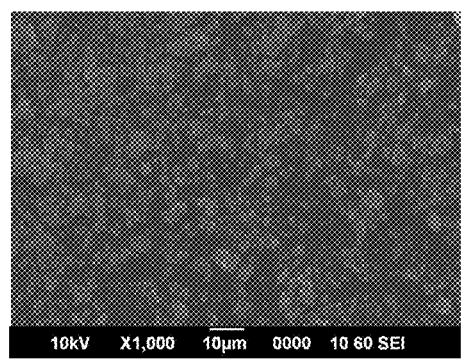
[FIG. 5]
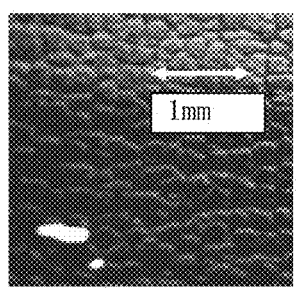

HYDROPHILIC THICKENER AND COSMETIC COMPOSITION

This application is a U.S. national stage application under 35 U.S.C. §371 of International Patent Application No. PCT/JP2014/065114 filed on Jun. 6, 2014, which claims the benefit of foreign priority to Japanese Patent Application No. JP 2013-136521 filed on Jun. 28, 2013. The entire contents of each of which is incorporated herein by reference.

TECHNICAL FIELD

The present invention relates to a hydrophilic thickener and a cosmetic composition using the thickener.

BACKGROUND ART

Acrylic acid-based carboxyl group-containing hydrophilic polymers as represented by carboxyvinyl polymers show excellent thickening property with a small amount of use, so that the carboxyl group-containing hydrophilic polymers have been widely used as thickeners in various industrial fields such as cosmetics and toiletries (see, Patent Publication 1). In addition, in the field of cosmetics, in order to further increase a fresh feel of use, a system in which an acrylamide-based thickener and sodium carbonate are used together has been also proposed (see, Patent Publication 2). However, as the amount used increases, there were some disadvantages that the structure is kinked, so that a phenomenon of flaking, so-called kink, is more likely to be caused. In order to solve the occurrence of this kink, a method of adding a high-molecular weight polyethylene glycol as a moisturizing polyhydric alcohol has also been proposed. However, there were some disadvantages that a sticky feel is more likely to be caused, and the transparency during the gelation would be also lowered (see, Patent Publication 3).

In addition, in order to thicken by using the carboxyvinyl polymers, it is necessary to first disperse the carboxyvinyl polymers in water, and thereafter neutralize the dispersion with an alkali such as sodium hydroxide to form a swollen gel. In this dispersing step, it is necessary to neutralize the carboxyvinyl polymer while carefully stirring the dispersion so as not to form a doughy mass, thereby requiring some time. In order to omit this neutralizing step, a thickener that is previously neutralized with an alkali so that a neutralizing step is not needed has been also proposed (see, Patent Publications 4 and 5).

PRIOR ART REFERENCES

Patent Publications

Patent Publication 1: Japanese Patent Laid-Open No. 2006-52319
Patent Publication 2: Japanese Patent Laid-Open No. 2007-284389
Patent Publication 3: Japanese Patent Laid-Open No. 2010-064986
Patent Publication 4: Japanese Patent Laid-Open No. Hei-4-218582
Patent Publication 5: Japanese Patent Laid-Open No. Hei-1-149805

SUMMARY OF THE INVENTION

Problems to be Solved by the Invention

However, the thickeners described in Patent Publications 4 and 5 are obtained by going through the steps of neutralization, concentration and separation, and the like in a solvent after firstly producing a water-soluble ethylenically unsaturated polymer, so that the production method is complicated and impractical. In addition, the properties of the polymer particles are not sufficiently controlled, so that doughy mass is likely to be formed, so that a disadvantage of requiring some time in dispersing the mixture, or the like is caused.

Further, when an acrylic acid-based carboxyl group-containing hydrophilic polymer is produced by a reversed phase suspension polymerization, the hydrophilic polymer is provided with polymerization stability with a surfactant, and the surfactant is preferred to have a relatively low HLB and be non-water-soluble. In that case, aqueous gels of the polymer turn into white turbid due to the influence of the surfactant remaining in the polymer, so that some disadvantages in transparency are caused.

An object of the present invention is to provide a hydrophilic thickener having excellent transparency and being less likely to cause kink, and a cosmetic composition using the thickener.

Means to Solve the Problems

As a result of intensive studies in order to solve the above-mentioned problems, the present inventors have found that a polymer obtainable by subjecting a water-soluble ethylenically unsaturated monomer to a reversed phase suspension polymerization in the presence of a specified surfactant is a hydrophilic thickener having excellent transparency and being less likely to cause kink. The present invention has been perfected thereby.

The present invention relates to:
[1] a hydrophilic thickener comprising a polymer obtainable by subjecting a water-soluble ethylenically unsaturated monomer to a reversed phase suspension polymerization in the presence of a polyoxyethylene polyoxypropylene alkyl ether; and
[2] a cosmetic composition containing a hydrophilic thickener as defined in the above [1].

Effects of the Invention

The hydrophilic thickener according to the present invention can be easily dispersed and thickened without neutralization, and has excellent transparency and less amount of kink, so that the hydrophilic thickener can be utilized in wide range of fields such as cosmetics.

BRIEF DESCRIPTION OF THE DRAWINGS

FIG. 1 An electron microscopic photograph of a hydrophilic thickener obtained in Example 1.
FIG. 2 A photograph of a 0.5% by mass aqueous gel of a hydrophilic thickener obtained in Example 1.
FIG. 3 A photograph of a 0.5% by mass aqueous gel of a hydrophilic thickener obtained in Comparative Example 1.
FIG. 4 An electron microscopic photograph of a carboxyvinyl polymer of Reference Example.
FIG. 5 A photograph of a kink that took place on an artificial leather in the evaluation of kink of a carboxyvinyl polymer of Reference Example.

MODES FOR CARRYING OUT THE INVENTION

The hydrophilic thickener according to the present invention comprises a polymer obtainable by subjecting a water-soluble ethylenically unsaturated monomer to a reversed phase suspension polymerization in the presence of a polyoxyethylene polyoxypropylene alkyl ether.

The method for polymerizing a water-soluble ethylenically unsaturated monomer according to a reversed phase suspension polymerization will be exemplified hereinbelow.

In a reversed phase suspension polymerization method, a polymerization takes place in a state that an aqueous solution of a water-soluble ethylenically unsaturated monomer is dispersed in a hydrophobic solvent with a surfactant.

The surfactant is used for stabilizing a suspending state during the polymerization, and the present invention has a great feature in the point that a polyoxyethylene polyoxypropylene alkyl ether is used as a surfactant. Since the polyoxyethylene polyoxypropylene alkyl ether is water-soluble, it is assumed that transparency of the aqueous gel is not impaired even when the polymer in which the polyoxyethylene polyoxypropylene alkyl ether remains is dissolved in water.

As the polyoxyethylene polyoxypropylene alkyl ether, a compound represented by the formula (I):

$$RO-(C_2H_4O)_m(C_3H_6O)_n-H \quad (I)$$

wherein R is an alkyl group having from 3 to 24 carbon atoms, m is integer of from 2 to 100, and n is an integer of from 2 to 100, is preferred.

In the formula, R is an alkyl group having from 3 to 24 carbon atoms, and preferably an alkyl group having from 4 to 18 carbon atoms. When the number of carbon atoms exceeds 24, it is not preferable because stability during the polymerization is lowered.

m which stands for the number of moles of ethylene oxide added is from 2 to 100, and preferably from 10 to 60. When it exceeds 100, it is not preferable because stability during the polymerization is lowered. In addition, n which stands for the number of moles of propylene oxide added is from 2 to 100, and preferably from 10 to 40. When it exceeds 100, it is not preferable because transparency during the gelation is worsened.

Ethylene oxide ($C_2H_4O$) and propylene oxide ($C_3H_6O$) may be added in a block form or a random form.

The polyethylene polyoxypropylene alkyl ether represented by the formula (I) include:
polyoxyethylene polyoxypropylene butyl ether [UNILUBE 50 MB-11 (m:9, n:10), UNILUBE 50 MB-26 (m:17, n:17), UNILUBE 50 MB-72 (m:30, n:30), UNILUBE 50 MB-168 (m:37, n:38) (hereinabove manufactured by NOF Corporation)];
polyoxyethylene polyoxypropylene cetyl ether [UNISAFE 10P-4 (m:10, n:4), UNISAFE 20P-4 (m:20, n:4), UNISAFE 5P-4 (m:5, n:4), UNISAFE 5P-8 (m:5, n:8), UNISAFE 10P-8 (m:10, n:8), UNISAFE 20P-8 (m:20, n:8) (hereinabove manufactured by NOF Corporation)];
polyoxyethylene polyoxypropylene lauryl ether [NONION A-10R (m:6, n:5), NONION A-13P (m:5, n:5), NONION A-25B (m:25, n:25) (hereinabove manufactured by NOF Corporation)];
polyoxyethylene polyoxypropylene stearyl ether [UNILUBE 10MS-250 KB (m:3, n:34), UNISAFE 34S-23 (m:34, n:23) (hereinabove manufactured by NOF Corporation)];
and the like.

The amount of the polyoxyethylene polyoxypropylene alkyl ether used is preferably 0.5 parts by mass or more, based on 100 parts by mass of the water-soluble ethylenically unsaturated monomer, from the viewpoint of controlling particle sizes during suspension, and increasing stability during the suspension to give a spherical polymer. In addition, the amount used is preferably 10 parts by mass or less, from the viewpoint of controlling stickiness of the surface of the hydrophilic thickener, and improving handling ability. Taking these viewpoints together, the amount of the polyoxyethylene polyoxypropylene alkyl ether used is preferably from 0.5 to 10 parts by mass, and more preferably from 1 to 5 parts by mass, based on 100 parts by mass of the water-soluble ethylenically unsaturated monomer.

The water-soluble ethylenically unsaturated monomer is not particularly limited, and it is preferable that the water-soluble ethylenically unsaturated monomer is at least one member selected from the group consisting of acrylic acid and salts thereof, methacrylic acid and salts thereof, 2-acrylamide-2-methylpropanesulfonic acid and salts thereof, acrylamide, methacrylamide, and N,N-dimethylacrylamide. Among these unsaturated monomers, acrylic acid and salts thereof and methacrylic acid and salts thereof, which are monomers having a carboxyl group, are more preferred, from the viewpoint of more likely to obtain sufficient thickening property, etc.

The concentration of the aqueous solution of the water-soluble ethylenically unsaturated monomer is preferably from 20 to 60% by mass or so.

When the water-soluble ethylenically unsaturated monomer has an acid group, as in (meth)acrylic acid, 2-(meth) acrylamide-2-methylpropanesulfonic acid or the like, a monomer of which acid group is previously neutralized with an alkaline neutralizing agent may be used as occasion demands. The alkaline neutralizing agent as described above is not particularly limited, and the alkaline neutralizing agent includes, for example, alkali metal salts such as sodium hydroxide and potassium hydroxide; ammonia, and the like. Especially these alkaline neutralizing agents may be used in a solution state in order to simplify the neutralization procedures. The above alkaline neutralizing agent may be used alone or in a combination of two or more kinds.

The degree of neutralization of the water-soluble ethylenically unsaturated monomer with the alkaline neutralizing agent is not particularly limited, and it is considered to be a degree of neutralization against all the acid groups owned by water-soluble ethylenically unsaturated monomers, and usually the degree of neutralization is preferably from 10 to 100% by mol, and more preferably from 20 to 80% by mol, from the viewpoint of thickening due to electrostatic repulsions of the polymer chain.

The hydrophobic solvent is preferably at least one petroleum-based hydrocarbon solvent selected from the group consisting of aliphatic hydrocarbons, alicyclic hydrocarbons, and aromatic hydrocarbons, from the viewpoint of safety and polymerization temperature.

The aliphatic hydrocarbon includes n-pentane, n-hexane, n-heptane, and the like. The alicyclic hydrocarbon includes cyclopentane, methylcyclopentane, cyclohexane, methylcyclohexane, and the like. The aromatic hydrocarbon includes benzene, toluene, xylene, and the like. Among them, at least one petroleum-based hydrocarbon solvent selected from n-hexane, n-heptane, cyclohexane, and toluene is preferably used as an industrially widely used solvent.

The amount of the hydrophobic solvent used is preferably from 100 to 200 parts by mass or so, based on 100 parts by mass of the aqueous solution containing the water-soluble ethylenically unsaturated monomer.

It is preferable that the polymerization is, for example, carried out in the presence of a polymerization initiator which is added to an aqueous solution of a water-soluble ethylenically unsaturated monomer. As the polymerization initiator, a usual radical initiator is preferably used. The radical initiator includes potassium persulfate, ammonium persulfate, sodium persulfate, azo-based initiators, and the like.

The amount of the polymerization initiator used is preferably 0.01 parts by mass or more, based on 100 parts by mass of the water-soluble ethylenically unsaturated monomer, from the viewpoint of obtaining the effects of accelerating the polymerization reaction. In addition, the amount used is preferably 0.5 parts by mass or less, from the viewpoint of controlling the progress of a vigorous polymerization reaction.

In addition, an internal crosslinking or post-crosslinking of the polymer may be carried out with a crosslinking agent. A crosslinking agent may be added to a reaction system before the initiation of polymerization or during the polymerization, or may be added after the termination of polymerization. The texture of the polymer can be controlled by internal crosslinking or post-crosslinking.

The crosslinking agent is preferably a compound having two or more polymerizable unsaturated groups and/or reactive functional groups. The reactive functional group is a functional group capable of forming a crosslinked structure by a reaction with a functional group such as a carboxyl group of a water-soluble ethylenically unsaturated monomer. Specific examples thereof include a glycidyl group, and the like. The crosslinking agent having two or more glycidyl groups include ethylene glycol diglycidyl ether, polyethylene glycol diglycidyl ether, and the like. The crosslinking agent having two or more polymerizable unsaturated groups includes N,N'-methylenebisacrylamide, ethylene glycol dimethacrylate, polyethylene glycol dimethacrylate, water-soluble sucrose allyl ethers and the like.

The amount of the crosslinking agent used is preferably from 0.1 to 0.5 parts by mass, based on 100 parts by mass of the water-soluble ethylenically unsaturated monomer.

The reaction temperature of the polymerization reaction differs depending upon the kinds of the polymerization initiator, and the like, and the reaction temperature usually is preferably from 20° to 110° C., and more preferably from 40° to 90° C., from the viewpoint of rapidly progressing the polymerization, and shortening the polymerization time, thereby increasing productivity, and easily removing heat of polymerization and smoothly carrying out the reaction. It is preferable that the reaction time is usually from 0.1 hours to 4 hours or so.

After the termination of the polymerization, water and a hydrophobic solvent are distilled off from a liquid reaction mixture by distillation or the like, and the residue is dried, whereby a dry product of the polymer usable as a hydrophilic thickener can be obtained.

In a case where the monomer used in the polymer usable as the hydrophilic thickener according to the present invention is previously neutralized, a dispersing step or a neutralizing step would be unnecessary, as in the case of a carboxyvinyl polymer, which is a crosslinked product of acrylic acid which is widely used as a thickener, so that the product can be easily thickened. Specifically, thickening can be realized in a short period of time by directly adding the polymer to a subject solution such as water or an alcohol solution while stirring the mixture.

Transparency of the gel required as raw materials for cosmetics is needed to be, in terms of transmittance of an aqueous gel at a concentration of 0.5% by mass, preferably 70% or more, and more preferably 90% or more. When the transmittance is less than 70%, there is a risk of worsening the transparency when used as cosmetics.

As to the transparency of the gel which can be evaluated by transmittance of light beam at 425 nm with an ultraviolet-visible spectrophotometer when filled in a silica glass cell having an optical path length of 1 cm, the aqueous gel at a concentration of 0.5% by mass having transmittance of 90% or more, which is of the same level as that of the conventional carboxyvinyl polymer, is obtained. The viscosity of the aqueous gel at a concentration of 0.5% by mass is preferably from 15,000 to 40,000 mPa·s, and preferably from 20,000 to 35,000 mPa·s, from the viewpoint of shape-retaining property and feel of use etc.

In addition, in the reversed phase suspension polymerization, the shapes and particle sizes of the polymer to be obtained can be easily controlled by a rotational speed, a w/o ratio or the like. It is preferable that the shapes of the hydrophilic thickener according to the present invention are controlled to a spherical form, and the particle size of the powder (median particle size) is preferably from 5 to 30 µm or so. A conventional carboxyvinyl polymer powder has an irregular particle shape and a particle size of 10 µm or less, and the gel particle size upon thickening is from 10 to 50 µm or so, which is small, whereas the thickener according to the present invention shows even a smoother feel and can be smoothly spread without causing kinks because the thickener is allowed to swell to a large size overall to an extent that the gel particle size upon thickening is, for example, from 30 to 200 µm or so, preferably from 80 to 180 µm, and the shapes of the particles are spherical.

Therefore, the present invention further provides a cosmetic composition containing a hydrophilic thickener according to the present invention. For example, a thickener according to the present invention can be dissolved in water or an aqueous alcohol solution to be used as a cosmetic composition or raw materials therefor. Cosmetics containing a hydrophilic thickener according to the present invention include powder foundations, liquid foundations, emulsions, lotions, liquid cosmetics, cleansing foams, hair setting agents, emollient creams, and the like. Among them, the thickener can be suitably used in cosmetics that require transparency, such as moisturizing gels, all-in-one gels, and lotions.

EXAMPLES

The present invention will be hereinbelow described more specifically by means of Examples, without intending to limit the present invention to these Examples.

As to hydrophilic thickeners described in Examples, (1) shape, (2) median particle size, (3) viscosity of aqueous gel, (4) transparency, (5) kink, and (6) texture were measured in accordance with the following methods.

(1) Shape

A hydrophilic thickener is observed with an electron microscope at a magnification of 1,000 folds.

(2) Median Particle Size

In 5 ml of hexane is dispersed 0.1 g of a hydrophilic thickener, a particle size distribution of the dispersion is then measured using a particle size distribution measurement instrument (SALD2000, manufactured by Shimadzu Corporation, using flow cell), and an average on a mass basis calculated from the particle size distribution obtained is defined as a median particle size.

(3) Viscosity of Aqueous Gel

In 298.5 g of ion-exchanged water is supplied 1.5 g of a hydrophilic thickener, and the mixture is stirred for 60 minutes under the conditions of 25° C. and 400 r/min, to prepare a 0.5% by mass aqueous gel of the hydrophilic thickener. The viscosity of the aqueous gel obtained is measured under the following conditions.

<Viscosity Measurement Conditions>

B-type viscometer: Vismetron VS-1H, manufactured by Shibaura Systems K.K.
Temperature: 25° C.
Rotor: No. 6
Rotational speed: 20 r/min (4) Transparency A silica glass cell having an optical path length of 1 cm is filled with 4.5 ml of the aqueous gel prepared in the measurement of the above (3), and bubbles are removed with a centrifuge (1800 r/min). Transmittance of the light beam at 425 nm is measured with an ultraviolet-visible spectrophotometer (UV-3150: manufactured by Shimadzu Corporation), thereby evaluating transparency.

(5) Kink 30 g of propylene glycol is added to 70 g of the aqueous gel prepared in the measurement of the above (3) to give a transparent gel. To an artificial leather cut into dimensions of a width of 2 cm×a length of 5 cm (Supplare, manufactured by Idemitsu Technofine) is added dropwise 0.5 g of the transparent gel obtained, and rubbed in thereon to dryness with a pointing finger. The procedures of rubbing-in are repeated 5 times, and a surface of the artificial leather is obtained each time. The kink is evaluated in accordance with the following evaluation criteria.

<Evaluation Criteria>

○(Good): White agglomerates (kinks) not being found
×(Poor): Some white agglomerates (kinks) being found (6) Texture (Sensory Test)

With respect to each of the aqueous gels obtained Examples and Comparative Examples, refreshing feel and lightness when the aqueous gel is applied to the back of the hand in a proper amount and spread with a finger by testers consisting of 5 each of males and females are evaluated as texture by the following criteria.

<Evaluation Criteria>

A: Refreshing feel and lightness are excellent.
B: Refreshing feel and lightness are slightly poor.
C: Refreshing feel and lightness are poor with sticky feel.

Example 1

A 1-L volume four-necked cylindrical, rounded bottom flask equipped with a stirrer, a reflux condenser and a nitrogen gas inlet tube was charged with 500 mL (340 g) of n-heptane.

On the other hand, a 500-mL volume Erlenmeyer flask was separately furnished, and 92 g of a 80% by mass aqueous solution of acrylic acid was added thereto. Thereto was added dropwise 54.9 g of a 30% by mass aqueous sodium hydroxide solution while cooling from the external to neutralize 40% by mol, and thereafter 0.04 g of 2,2'-azobis(2-methylpropionamidine) dihydrochloride as a polymerization initiator, 0.28 g of a water-soluble sucrose allyl ether as a crosslinking agent, and 75 g of ion-exchanged water as a concentration adjuster were further added thereto to dissolve, thereby preparing a 47% by mass aqueous solution of a partially neutralized acrylic acid (222.22 g).

Next, an entire amount of the above aqueous solution of a partially neutralized acrylic acid was added to the above four-necked cylindrical, rounded bottom flask under conditions of a rotational speed of 800 r/min to disperse, and 2.76 g of a polyoxyethylene polyoxypropylene stearyl ether (UNISAFE 34S-23 (manufactured by NOF Corporation)) was added thereto.

After heating the system, the internal of the system was replaced with nitrogen, and a polymerization reaction was carried out for about 0.5 hours while keeping a bath temperature to 60° C. After the termination of polymerization reaction, a slurry containing the crosslinked product of the polyacrylate salt obtained was dried at 120° C. for 2 hours to give 94.2 g of a hydrophilic thickener.

The evaluation results of the hydrophilic thickener obtained are shown in Table 1. FIG. 1 shows an electron microscopic photograph of a hydrophilic thickener obtained in Example 1, and FIG. 2 shows a photograph of a 0.5% by mass aqueous gel of the hydrophilic thickener.

Example 2

The same procedures as in Example 1 were carried out except that 2.76 g of a polyoxyethylene polyoxypropylene butyl ether (UNILUB 50 MB-168 (manufactured by NOF Corporation)) was used in place of the polyoxyethylene polyoxypropylene stearyl ether, to give 94 g of a hydrophilic thickener. The evaluation results of the hydrophilic thickener obtained are shown in Table 1.

Comparative Example 1

The same procedures as in Example 1 were carried out except that 2.76 g of sorbitan monopalmitate (surfactant; NONION PP-40R (manufactured by NOF Corporation)) was used in place of the polyoxyethylene polyoxypropylene stearyl ether, to give 94.1 g of a hydrophilic thickener. The evaluation results of the hydrophilic thickener obtained are shown in Table 1. FIG. 3 shows a photograph of a 0.5% by mass aqueous gel of a hydrophilic thickener obtained in Comparative Example 1.

Comparative Example 2

The same procedures as in Example 1 were carried out except that 2.76 g of hexaglycerol monostearate (surfactant; RYOTO-Polyglyester HS-9 (manufactured by Mitsubishi-Kagaku Foods Corporation)) was used in place of the polyoxyethylene polyoxypropylene stearyl ether. However, lumpy mass was formed, so that a hydrophilic thickener was not obtained.

Comparative Example 3

The same procedures as in Example 1 were carried out except that 2.76 g of polyethylene glycol-polypropylene glycol-polyethylene glycol (PLONONE 102 (manufactured by NOF Corporation)) was used in place of the polyoxyethylene polyoxypropylene stearyl ether. However, lumpy mass was formed, so that a hydrophilic thickener was not obtained.

Reference Example

As a carboxyvinyl polymer, 3.2 g of AQUPEC 504E (manufactured by Sumitomo Seika Chemicals Co., Ltd.) was dispersed in 95.5 g of ion-exchanged water over 15 minutes, so as not to form doughy mass, 1.2 g of sodium hydroxide was then added to the mixture, and the mixture was stirred with a hand-mixer (500 r/min) for 20 minutes, to give a hydrophilic thickener. The evaluation results are shown in Table 1. FIG. 4 shows an electron microscopic photograph of a carboxyvinyl polymer of Reference Example, and FIG. 5 shows a photograph of a kink that took place on an artificial leather in the evaluation of kink of a carboxyvinyl polymer of Reference Example.

TABLE 1

|  | Shape | Median Particle Size [μm] | Viscosity of Aqueous Gel [mPa·s] | Transparency [%] | Kinks 1st | 2nd | 3rd | 4th | 5th | Texture |
|---|---|---|---|---|---|---|---|---|---|---|
| Ex. 1 | Spherical | 10 | 35,000 | 99 | ○ | ○ | ○ | ○ | ○ | A |
| Ex. 2 | Spherical | 15 | 25,000 | 94 | ○ | ○ | ○ | ○ | ○ | A |
| Comp. Ex. 1 | Spherical | 15 | 27,000 | 5 | ○ | ○ | ○ | x | x | A |
| Comp. Ex. 2 | Lumpy Mass | — | — | — | — | — | — | — | — | — |
| Comp. Ex. 3 | Lumpy Mass | — | — | — | — | — | — | — | — | — |
| Ref. Ex. | Irregular | 1 | 33,000 | 99 | ○ | x | x | x | x | C |

It can be seen from the above results that the spherical hydrophilic thickeners of Examples 1 and 2, obtained according to reversed phase suspension polymerization using polyoxyethylene polyoxypropylene alkyl ether have excellent transparency and less likelihood of causing kinks, and have excellent texture, as compared to those of Comparative Examples 1 to 3 and Reference Example.

INDUSTRIAL APPLICABILITY

The hydrophilic thickener according to the present invention can be used in the fields of cosmetics such as powder foundations, liquid foundations, emulsions, lotions, liquid cosmetics, moisturizing gel, all-in-one gels, cleansing foams, hair setting agents, emollient creams; toiletries, sundries, and the like.

The invention claimed is:

1. A hydrophilic thickener comprising a polymer obtained by subjecting a water-soluble ethylenically unsaturated monomer to a reversed phase suspension polymerization in the presence of a polyoxyethylene polyoxypropylene alkyl ether;
wherein transmittance of light beam at 425 nm for an aqueous gel of the hydrophilic thickener at a concentration 0.5% by mass is 90% or more.

2. The hydrophilic thickener according to claim 1, wherein the water-soluble ethylenically unsaturated monomer is at least one member selected from the group consisting of acrylic acid and salts thereof, methacrylic acid and salts thereof, 2-acrylamide-2-methylpropanesulfonic acid and salts thereof, acrylamide, methacrylamide, and N,N-dimethylacrylamide.

3. The hydrophilic thickener according to claim 1 or 2, wherein the polyoxyethylene polyoxypropylene alkyl ether is a compound represented by the formula (I):

$$RO-(C_2H_4O)_m(C_3H_6O)_n-H \quad (I)$$

wherein R is an alkyl group having from 3 to 24 carbon atoms, m is an integer of from 2 to 100, and n is an integer of from 2 to 100.

4. A cosmetic composition comprising a hydrophilic thickener as defined in claim 1.

5. A hydrophilic thickener consisting essentially of a polymer obtained by subjecting a water-soluble ethylenically unsaturated monomer to a reversed phase suspension polymerization in the presence of a polyoxyethylene polyoxypropylene alkyl ether;
wherein transmittance of light beam at 425 nm for an aqueous gel of the hydrophilic thickener at a concentration 0.5% by mass is 90% or more.

6. The hydrophilic thickener according to claim 5, wherein the water-soluble ethylenically unsaturated monomer is at least one member selected from the group consisting of acrylic acid and salts thereof, methacrylic acid and salts thereof, 2-acrylamide-2-methylpropanesulfonic acid and salts thereof, acrylamide, methacrylamide, and N,N-dimethylacrylamide.

7. The hydrophilic thickener according to claim 5, wherein the polyoxyethylene polyoxypropylene alkyl ether is a compound represented by the formula (I):

$$RO-(C_2H_4O)_m(C_3H_6O)_n-H \quad (I)$$

wherein R is an alkyl group having from 3 to 24 carbon atoms, m is an integer of from 2 to 100, and n is an integer of from 2 to 100.

8. A cosmetic composition comprising a hydrophilic thickener as defined in claim 5.

* * * * *